US005094228A

United States Patent [19]

Reinert

[11] Patent Number: 5,094,228

[45] Date of Patent: Mar. 10, 1992

[54] APPARATUS FOR TREATMENT OF THE BACK

[76] Inventor: Otto C. Reinert, 2024 Long Gate Ct., Chesterfield, Mo. 63017

[21] Appl. No.: 555,725

[22] Filed: Jul. 19, 1990

[51] Int. Cl.[5] .......... A61F 5/00

[52] U.S. Cl. .......... 606/243

[58] Field of Search .......... 128/68-75, 128/78

[56] References Cited

U.S. PATENT DOCUMENTS

| | | | |
|---|---|---|---|
| 1,080,297 | 12/1913 | Pitts et al. . | |
| 1,915,841 | 6/1933 | Warner . | |
| 2,590,670 | 3/1952 | Anderson | 128/71 |
| 2,693,796 | 11/1954 | Warner | 128/33 |
| 2,910,061 | 10/1959 | Rabjohn | 128/75 X |
| 3,117,572 | 1/1964 | Wright | 128/75 |
| 3,153,411 | 10/1964 | Unks | 128/75 |
| 3,683,900 | 8/1972 | Alessi et al. | 128/75 |
| 3,771,518 | 12/1972 | Wright | 128/75 |
| 3,915,160 | 10/1975 | Lode et al. | 128/69 |
| 4,114,611 | 9/1978 | Lyle et al. | 128/75 |
| 4,130,250 | 12/1978 | Evans et al. | 128/75 X |
| 4,205,665 | 6/1980 | Burton | 128/68 |
| 4,524,763 | 6/1985 | Eberling, Jr. | 128/75 |
| 4,569,340 | 2/1986 | Burton | 128/75 |
| 4,579,109 | 4/1986 | Lundblad | 128/72 |
| 4,603,689 | 8/1986 | Horner | 128/75 |
| 4,762,134 | 8/1988 | Gala | 128/781 |

*Primary Examiner*—Robert Bahr
*Assistant Examiner*—J. Doyle
*Attorney, Agent, or Firm*—Senniger, Powers, Leavitt & Roedel

[57] ABSTRACT

Apparatus for treatment of the back is disclosed. The apparatus includes a table for supporting a patient lying on this back. Traction units are provided to place the patient's spine in traction, one side independent of the other, as he lies on the table. A back support is positioned underneath the patient's back for engagement with an area of the back to be treated. The back support is connected to a lift mechanism to move the back support laterallly toward one side or the other and vertically and in an inclined direction with is the resultant of a horizontal and vertical motion.

20 Claims, 6 Drawing Sheets

APPARATUS FOR TREATMENT OF THE BACK

BACKGROUND OF THE INVENTION

This invention relates generally to apparatus for treatment of the back, and more particularly to such apparatus capable of carrying out therapeutic manipulations of the back.

Many back ailments may be treated by traction, by passively orienting the spine in an extending position (i.e., upward arching of the back from a supine position), by lateral bending of the spine, or by some combination of the foregoing. A common cause of low back pain and disability is the partial displacement of the disc nucleus from between adjacent vertebrae such that the disc bulge impinges on nerves in the spinal area. As a result the adjacent vertebrae no longer assume a position relative to each other of general vertical alignment when the person's back is erect, but rather the intervertebral disc space takes on a wedge shaped orientation. Manipulative techniques, such as those described above, may be used to facilitate returning the disc to its proper attitude between the adjacent vertebrae such that the vertebrae resume their normal alignment. However, in the absence of any mechanical aid, such techniques of manipulation require a high degree of physical strength and dexterity beyond the capacities of many therapists. Furthermore, in complicated and severe cases, a combination of forces must be applied in multiple directions, requiring the participation of several persons.

There are presently machines which may carry out some of the necessary manipulations for back treatment. It has been found that manipulations of the back which place the spine in extension and/or traction have therapeutic affects on spinal disorders and other back ailments. However, existing machines lack the ability to combine controlled traction with manipulation of the back over the full range of positions of the spine, from purely lateral bending to pure extension and points in between. Further, these machines do not provide for applications of brief, but strong thrusts to the body important to successful treatment of many back ailments.

SUMMARY OF THE INVENTION

Among the several objects of the present invention may be noted the provision of apparatus for treatment of the back which exerts a controlled combination of traction upon the spine and a secondary force tending to arrange the spine laterally, in a direction placing the spine in extension, or in a direction with is the resultant of a lateral and extending motion; the provision of such apparatus which applies an impulse to a selected area of the back to be treated; the provision of such apparatus which may apply independent amounts of traction to opposing sides of the body; and the provision of such apparatus which allows numerous manipulations of the body to be carried out by a single therapist.

Generally, apparatus for treatment of the back constructed according to the principles of the present invention comprises support means for supporting a patient lying on his back and traction means for placing the patient's spine in traction. A back support is adapted to be positioned underneath the patient's back. Means is provided for effecting movement of the back support laterally toward one side or the other and vertically and in an inclined direction which is the resultant of a lateral and vertical movement.

Other objects and features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE PREFERRED EMBODIMENTS

Figure 1:
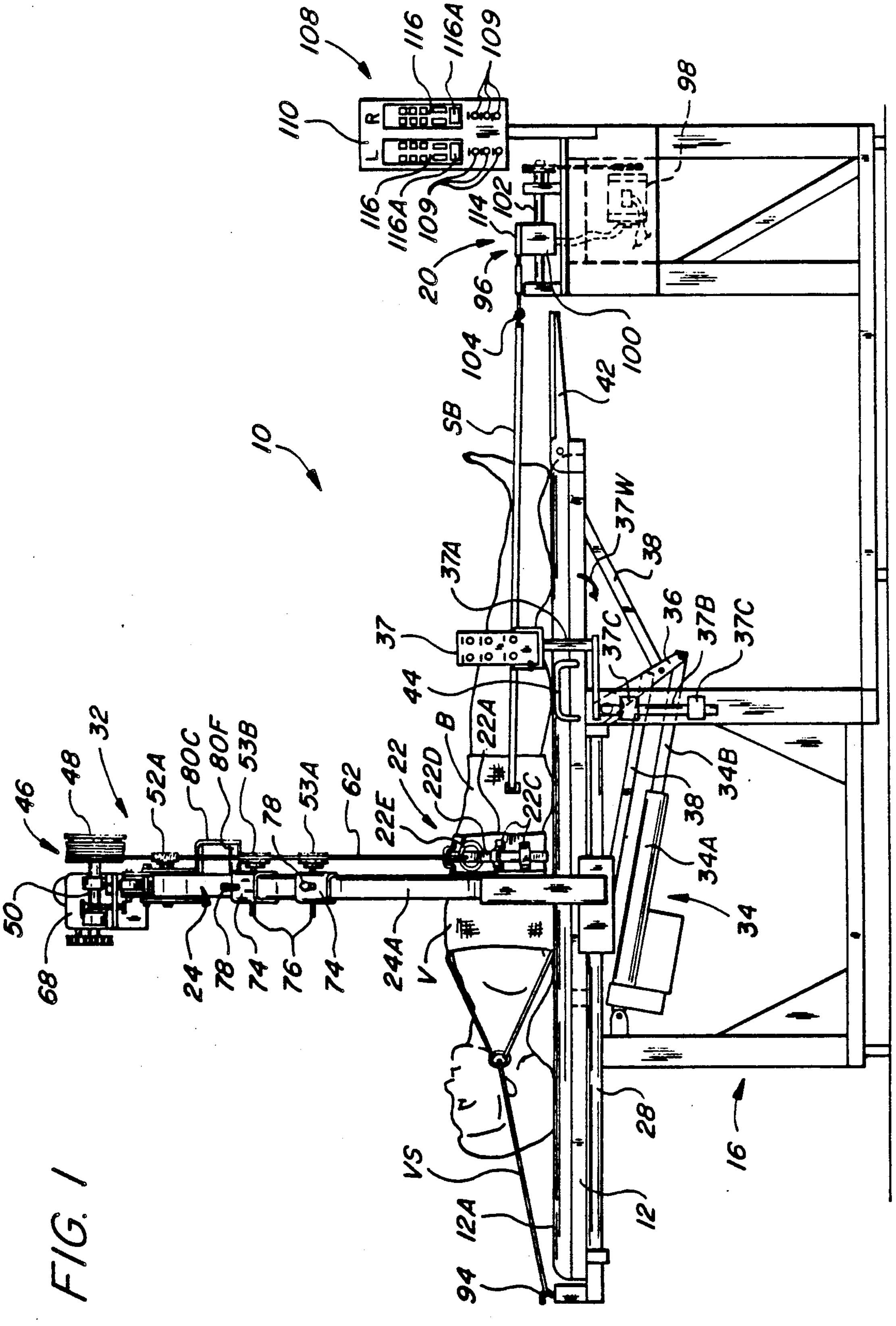
FIG. 1 is a side elevation of apparatus constructed according to the principles of the present invention.
Figure 2:
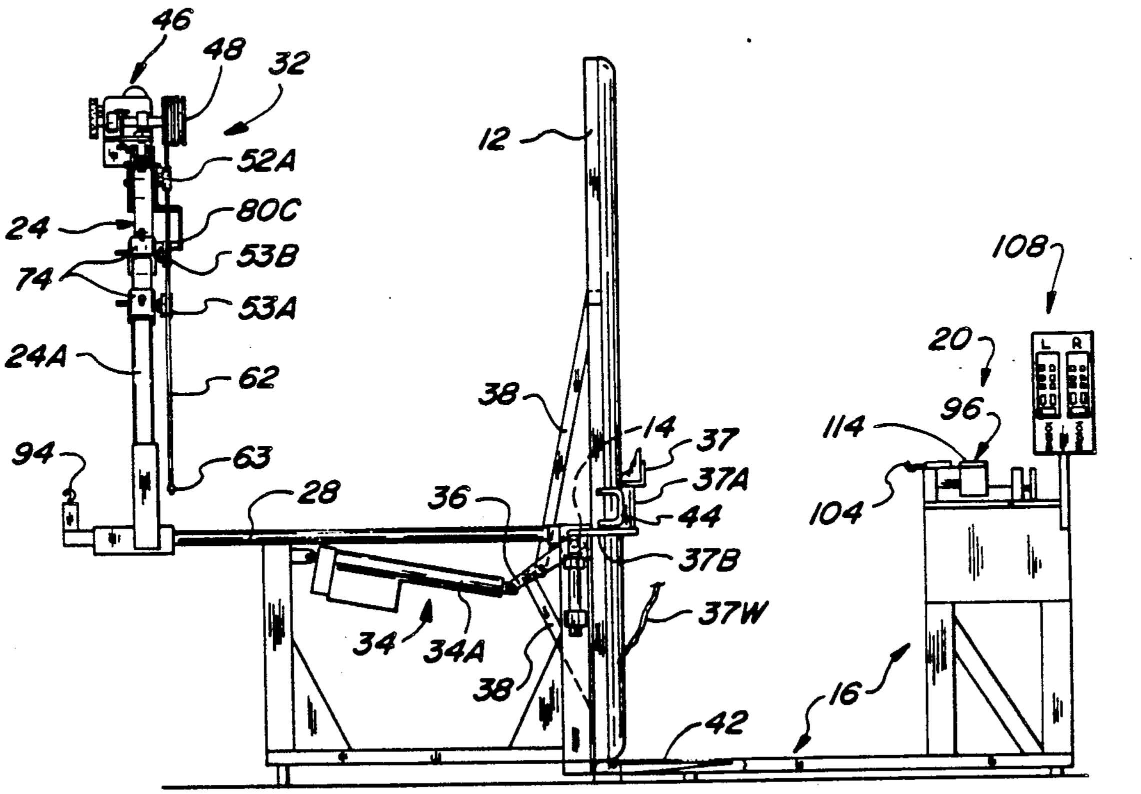
FIG. 2 is a side elevation of the apparatus, showing a table of the apparatus in its vertical position.
Figure 3:
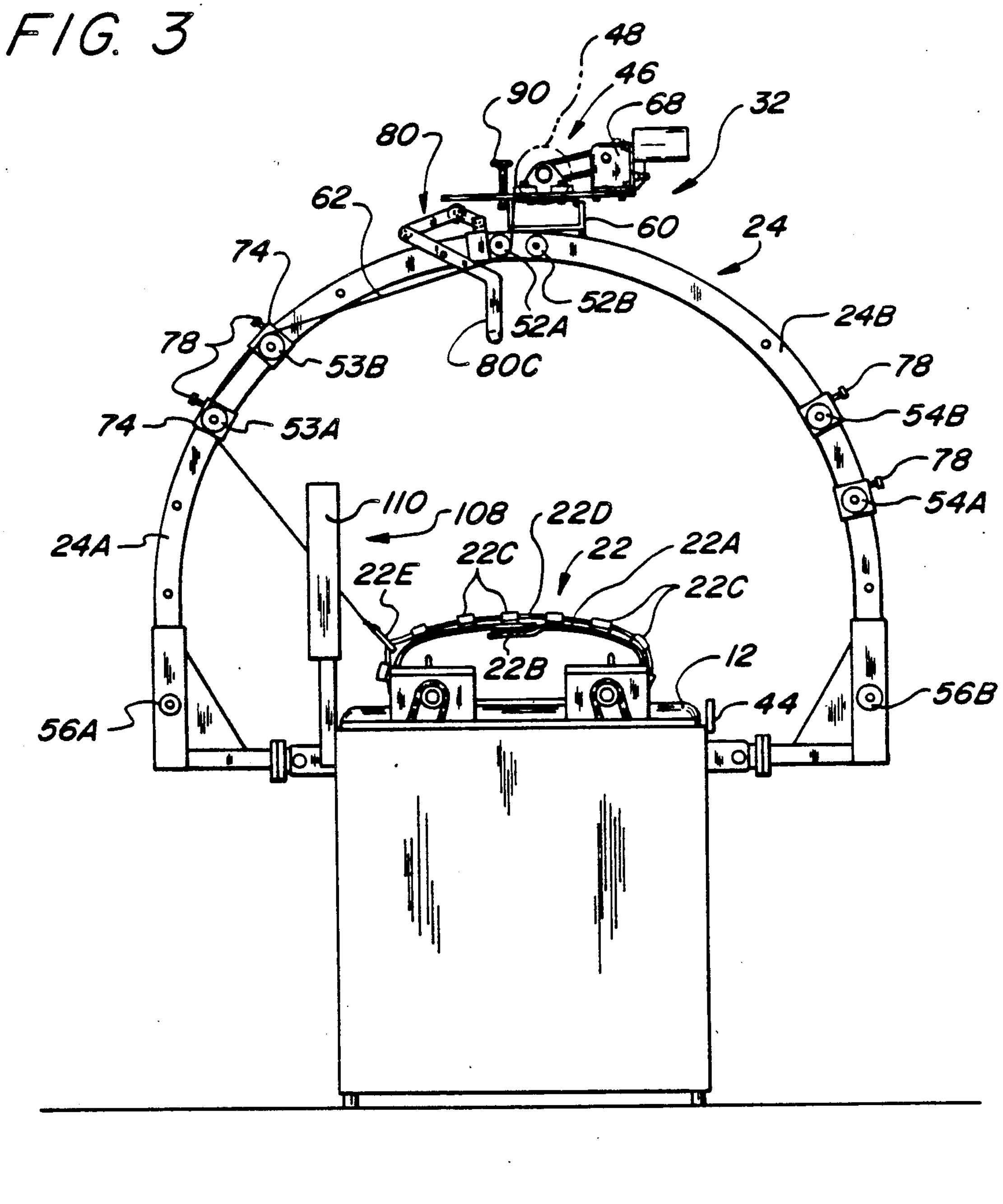
FIG. 3 is a right end elevation of the apparatus.

Referring now to the drawings, and more particularly to FIG. 1, apparatus, indicated generally at 10, is shown to comprise a table (support means) having a padded upper surface 12A adapted to support a patient's body P in a supine position. The patient's arm has not been illustrated in FIG. 1 in order to show details of the apparatus. The table 12 is pivotally mounted by a shaft 14 on a frame generally indicated at 16 (FIG. 2). Traction means 20 (FIG. 3) is provided for placing the patient's spine in traction, and a sling-like back support 22 is adapted to be positioned underneath the patient's back. An arch shaped support member 24 extending generally transversely over the table 12 has a first leg 24A disposed generally adjacent one side of the table and a second leg 24B disposed generally adjacent the laterally opposite side of the table (FIG. 3). The support member 24 is slidably mounted on rods 28 (FIG. 1) on either side of the table 12 for movement longitudinally of the table. The support member 24 may be locked in a specific position by suitable means (not shown). Means, indicated generally at 32 (FIGS. 1-3), for effecting movement of the back support 22 laterally toward one side or the other and vertically and in an inclined direction which is the resultant of a horizontal and vertical motion is supported by the support member 24.

To facilitate positioning a patient, who may be in pain and have little lower back flexibility, in a supine position on the table 12, the table is adapted to pivot from its horizontal position shown in FIG. 1 to a vertical position shown in FIG. 2. A cylinder 34 (FIG. 1), including a barrel 34A connected to the frame 16 and a rod 34B, is provided for pivoting the table. The rod 34B is telescopically received in the barrel 34A and is connected to a lever arm 36 extending from the shaft 14. Retraction of the rod 34B into the barrel 34A of the cylinder pivots the table 12 with respect to the frame 16 from the horizontal position shown in FIG. 1 to the vertical position shown in FIG. 2. Activation of the cylinder 34 to extend and retract the rod 34B is controlled from a control box 37. A support column 37A projecting downwardly from the control box 37 is attached to an L-shaped bracket 37B clamped to the frame 16 by suitable fasteners 37C. The bracket 37B may pivot about a vertical axis over a range of approximately 160°. The support column 37A may also pivot on its longitudinal axis with respect to the bracket 37B. Therefore, the position of the control box 37 may be easily adjusted so as to be accessible to the operator from different positions.

Bracing bars 38 connected at one end to the lever arm 36 and at an opposite end to the frame 16 reinforce the lever arm. Prior to pivoting to the vertical position, the support member 24 must be moved to the head of the table 12 so that the table may swing through the support member without engaging it. A safety switch (not shown) disables the controls from being operable to swing the table 12 to its vertical position unless the support member 24 is located at the extreme head of the table (FIG. 2). In addition, a platform 42 pivotally mounted on the table 12 is swung from its position in the plane of the table to a position perpendicular to the table where it is releasably locked. In the table's vertical position, the patient may stand on the platform 42 with his back to the table. Extension of the cylinder rod 34B then swings the table 12 back to its horizontal position with the patient now laying on the table in a supine position. The patient may grasp handles 44 mounted on the sides of the table 12 to stabilize himself as the table pivots.

Figure 4:
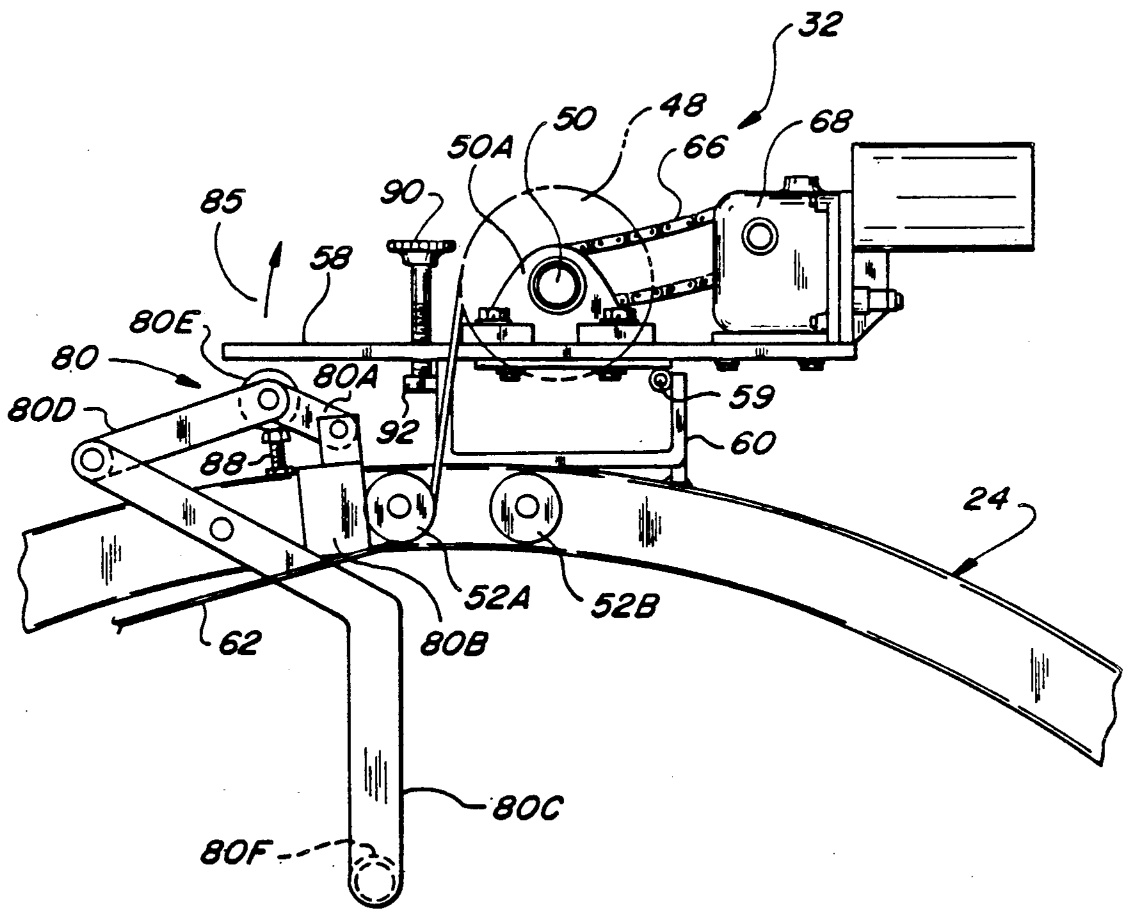
FIG. 4 is a fragmentary right end elevation of the apparatus showing a lift mechanism and impulse means.

The means 32 for effecting movement of the back support 22 comprises a lift mechanism, indicated generally at 46, which includes a drum 48 mounted for rotation on a shaft 50 at the top of the support member 24. The means 32 for effecting movement further includes guide members which comprise first pulley means on the first leg 24A, and second pulley means on the second leg 24B. As shown in FIG. 3, the first pulley means includes fixed pulley 52A mounted at the top of the support member 24 below the drum 48, and adjustable pulleys 53A and 53B. The second pulley means includes fixed pulley 52B mounted at the top of the support member 24 below the drum 48, and adjustable pulleys 54A and 54B. The first and second pulley means further include fixed pulleys, 56A and 56B, mounted on the support member 24 at the lower end of each leg 24A, 24B. The pulleys are adapted to guide the back support 22 as it is raised and lowered by the lift mechanism 46. The use of fixed pulleys 56A, 56B will be explained in more detail below. As shown in FIG. 4, the drum shaft 50 is mounted by suitable bearing members 50A on a platform 58. The platform is attached by a hinge 59 to a bracket 60 which is mounted on the support member 24. The drum 48 holds a length of cable 62, which constitutes cable means in this embodiment. The cable 62 is adapted to extend from the drum 48, under fixed pulley 52A or 52B, and over either pulleys 53A and 53B on the first leg 24A of the support member, or pulleys 54A and 54B on the second leg 24B of the support member.

The cable 62 has a clasp 63 at its free end for connection to the back support 22. The back support 22 includes an inner belt 22A which is made of strong, flexible material with a padded area inside at its center to concentrate force to a specific spinal level. The inner belt 22A is wrapped around the patient at the spinal level to be treated and secured by suitable fasteners 22B, such as a hook and loop type fastener, known by the trademark VELCRO. The inside belt 22A has a plurality of loops 22C attached to its outer surface. An outer belt 22D, also made of strong, flexible material, extends around the patient's body through the loops 22C and its free ends are secured together by a suitable fastener such as a buckle 22E. A heavy metal ring 23 is secured to the patient by the outer belt 22D, which passes through the center of the ring. The ring may slide lengthwise of the outer belt between adjacent loops 22C. The clasp 63 of the cable 62 is connected to the metal ring 33.

As shown in FIG. 3, the drum 48 is positioned so that the edge of the drum from which the cable 62 extends is laterally centered over the table 12. The drum shaft 50 is connected by a chain 66 to an electric motor 68 which may be energized and de-energized from control box 37. The motor 68 may rotate the drum 48 so as to reel in the cable 62 to raise the back support 22, or to let out cable to lower the back support.

Figure 7:
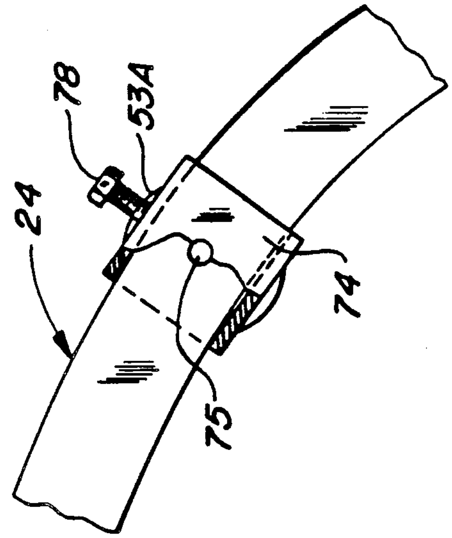
FIG. 7 is a fragmentary left end elevation of a support member of the apparatus showing an adjustable guide member, part of which is broken away to reveal a detent hole.

The pulleys (53A, 53B, 54A, 54B) are mounted on tubular sleeves 74 of rectangular cross section which may slide lengthwise along the legs of the support member 24. In this embodiment, it is usually the lower of the two pulleys shown on each leg (53A or 54A) which is adjusted for the purpose of selecting the direction of motion of the back support 22. The primary purpose of the upper pulleys (53B or 54B) is to restrict the location of the cable between the drum 48 and the lower pulleys to generally along the legs 24A, 24B, thus keeping the cable away from the patient. As shown in FIG. 7, holes 75 in the legs 24A, 24B are provided every 15° for receiving a detent pin 76 attached to the sleeve to hold the pulleys 53, 54 in a selected position of adjustment. Of course detent holes 75 may be provided more or less frequently than 15° and still fall within the scope of the present invention. To further secure the pulley's position, a bolt 78 threadably received through the sleeve 74 may be tightened against the support member 24.

To raise the back support 22 vertically, the cable 62 is made to extend directly from the drum 48 to the back support. If a pure lateral movement is required, the cable 62 is passed under pulley 52A or 52B, over the pulleys 53A, 53B or the pulleys 54A, 54B (depending upon the chosen lateral direction), and under the corresponding fixed pulley, 56A or 56B, before being attached to the back support 22. In this configuration, the back support 22 will be pulled to one side or the other of the table 12 without being raised from the table. To achieve motion in an inclined direction along a line which is the resultant of a vertical and lateral movement of the back support 22, the lower of the two pulleys, 53A or 54A, on the selected leg, 24A or 24B, of the support member 24 is positioned at the desired angle and locked into place. The cable 62 is made to extend under the fixed pulley, 52A or 52B, over the upper pulley, 53B or 54B, and the lower pulley, 53A or 54A, to the ends of the back support 22 such that activation of the lift mechanism 46 will cause the back support to move in the preselected direction as guided by the pulleys. Thus it may be seen that through selection of the pulleys to be used and/or by adjustment of the position of the pulleys, the therapist may choose any direction of travel for the back support 22 ranging at 15° intervals over nearly 180°, and lying in a plane parallel to the plane of the support member 24.

The lift mechanism 46 described above provides for sustained displacement of the back support 22 and hence the patient's body P. Impulse means, indicated generally at 80 (FIG. 5), is adapted to selectively actuate a brief, small magnitude displacement of the back support 22 to temporarily displace an area of the patient's back engaged by the back support. As shown in FIG. 4, the impulse means 80 comprises a linkage (pivoting means) mounted on the support member 24 under one end of the platform 58 mounting the drum 48. The platform 58, mounted by a hinge 59 on the bracket 60, may pivot with respect to the bracket and support member 24. The linkage includes a camming link 80A (FIG. 6) pivotally mounted at one end to a base 80B mounted on the support member 24. A lever 80C pivotally mounted on the support member 24 is connected to the other end of the camming link 80A by a cross link 80D. A roller 80E having a generally horizontal axis of rotation is connected to the linkage at the joint of the camming link 80A and the cross link 80D. The roller 80E is considered as an extension of the camming link 80A in this embodiment.

By grasping a handle 80F of the lever 80C and pulling the lever 80C in the direction indicated by arrow 84 in FIG. 4, the camming link 80A is caused to pivot over the base 80B. A pin 88 is provided to position the joint of the cross link 80D and the camming link 80A to prevent jamming of the linkage. In the course of its arcuate path over the base 80B, the roller 80E briefly engages the underside of the platform 58 which pivots on its hinge 59 thereby displacing the platform 58, and the drum 48 mounted thereon, slightly upwardly in the direction indicated by arrow 85. This unsustained, small magnitude displacement of the platform 58 and drum 48 is transmitted through the cable 62 to the back support 22, resulting in a like displacement of the back support against the portion of the patient's back engaged by the back support. Because the impulse is transmitted through the cable 62, the direction of the impulse is the same as the direction set for the movement of the back support 22 by the lift mechanism 46 previously described. The amount of displacement of the platform 58 and thus the back support 22 is controlled by positioning the underside of an edge of the platform nearest the camming link 80A closer to (for greater displacement) or farther away from (for lesser displacement) the roller 80E on the camming link. To this end, a set screw 90 is received through and threadably engages the platform 58. The bottom of the set screw 90 rests on an ear 92 projecting laterally outwardly from the bracket 60 such that turning the screw pivots the platform on its hinge 82. Thus, by turning the set screw 90 to vary the length of the screw between the ear 92 and the underside of the platform 58, the position of the underside of the platform relative to the camming link roller 80E may be adjusted.

Figure 5:
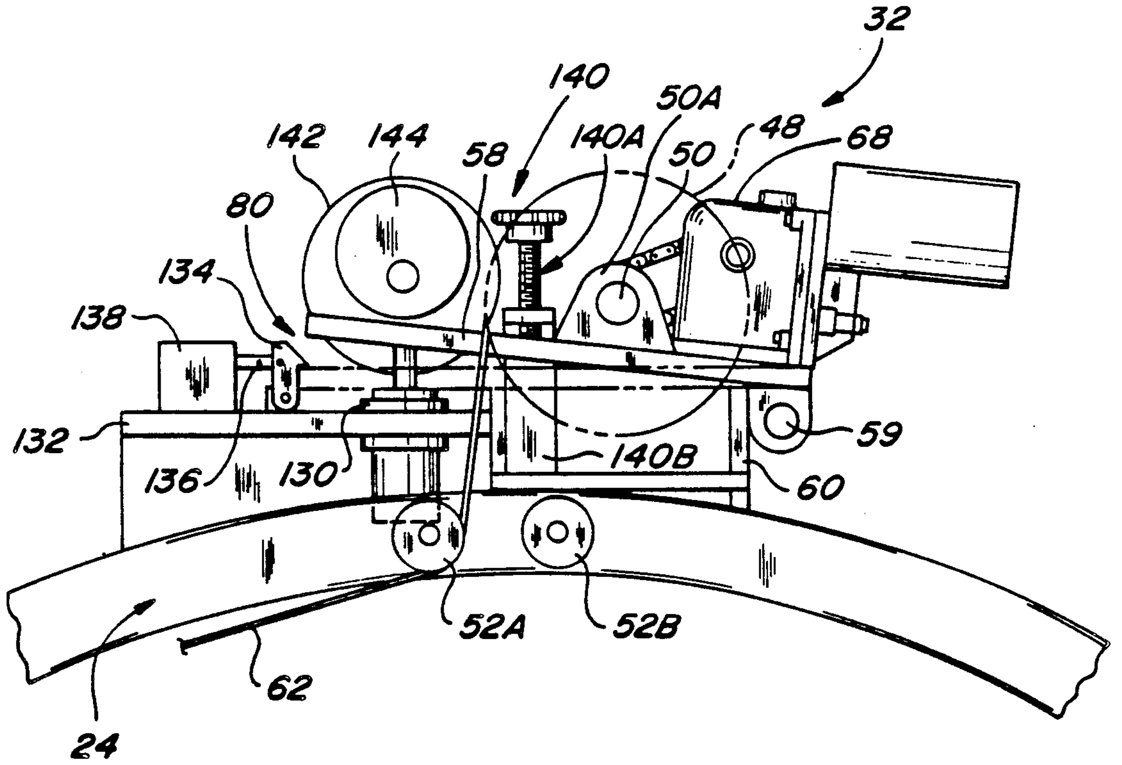
FIG. 5 is a fragmentary right end elevation of the apparatus showing an alternate embodiment of the impulse means.
Figure 6:
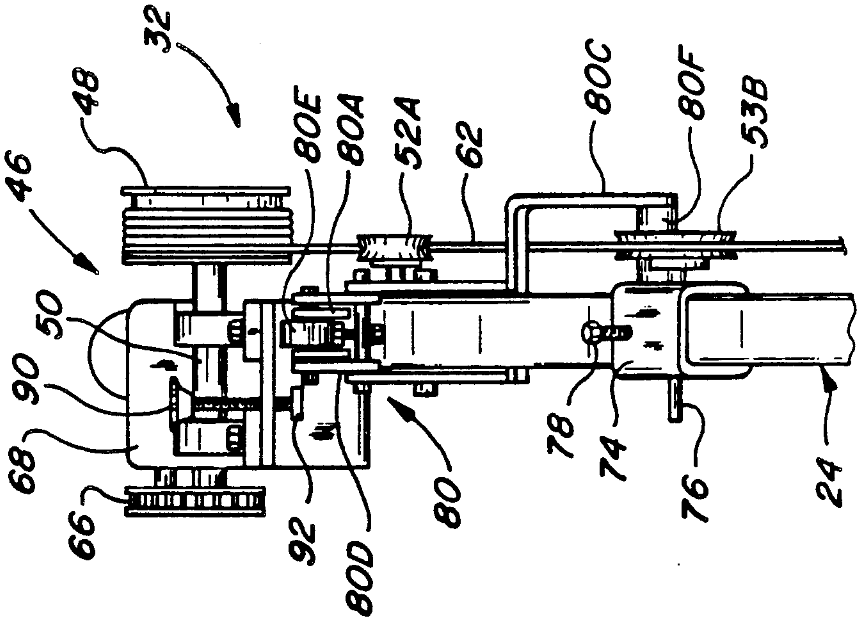
FIG. 6 is a fragmentary side elevation of the apparatus showing the lift mechanism and the impulse means.

An alternative embodiment of the impulse means 80 is shown in FIG. 5 to comprise spring means 130 (a nitrogen gas spring in this embodiment) mounted on a bracket 132 attached to the support member 24 and attached to the end of the platform 58 opposite its hinge connection 59 with the bracket 60. As shown in phantom in FIG. 5, the end of the platform 58 is held down, compressing the spring means 130, by a locking pin 134 pivotally attached to the bracket 132. The locking pin 134 is connected by a link 136 to a lock release mechanism 138 operable from a control (not shown) to rapidly pull back the link 136 and swing out the upper end of the locking pin 134 to release the end of the platform 58 and the spring means 130. The impulse means 80 may be constructed for manual release of the locking pin 134 (not shown), such as by lengthening the locking pin below its pivot so that it may be easily reached. In that event, the lock release mechanism 138 would not be present. The platform 58 is pivoted rapidly upwardly by the spring means 130 to a raised position, shown in solid lines in FIG. 5. The rapid upward pivoting of the platform produces a small magnitude displacement of the drum and hence the back support 22 substantially as described above in regard to the first embodiment of the impulse means 80. An adjustable stop indicated generally at 140 (FIG. 5) is provided for engaging the platform 58 to limit its upward motion. The stop 140 includes a bolt 140A threadably received through the upper end of a support 140B mounted on the support member 24. The distance the platform 58 may swing upwardly is reduced by turning the bolt 140B to increase the length of bolt projecting downwardly from the upper end of the support 140B, and increased by turning the bolt to lessen the length of bolt projecting downwardly from the upper end of the support. The impulse means 80 is automatically reset by activation of a motor 142 mounted on the bracket 132 which rotates a cam 144 a single revolution. The cam 144 engages the end of the platform 58 on the top side thereof, pushing the platform downward against the beveled upper end of the locking pin 134. The locking pin 134 snaps over the end of the platform 58, relocking the platform and holding the spring means 130 in its compressed position.

As will be described more fully below, beneficial results may be obtained by the combination of the forces applied to the patient's body P by the back support 22 in a plane transverse to the body, with traction which acts longitudinally of the body. To this end, the patient is placed in a thoracic vest V having straps VS leading from it which are attached to the table 12 by hooks 94 located at the head of the table (FIG. 1). A pelvic belt B having a pair of straps SB, one on each side, is also worn by the patient. Means for placing the patient's spine in traction 20 includes a pair of traction units 96 located at the foot of the table 12 and mounted on a portion of the frame 16 (FIG. 3). The traction units 96 each comprise a motor 98 (shown in hidden lines in FIG. 1) and a sled member 100 attached to a ball screw 102. The motors 98 turn the ball screws 102 to actuate motion of the sled members 100 along a line generally parallel to the longitudinal extension of the table 12. The sled members 100 each have hooks 104 for connecting one of the straps extending from the pelvic belt B to the sled member.

Control means, indicated generally at 108 (FIG. 1), is provided for independently controlling the amount of traction applied by each (left and right) traction unit 96. The control means includes control buttons 109 for each traction unit 96 which are incorporated into a control panel 110 mounted on a portion of the frame 16. The buttons 109 may be depressed to energize one or both of the motors 98 to apply or release traction. Means for detecting the traction applied by each traction unit 96 comprises in this embodiment a load cell 114 on each sled member 100, and means for displaying the load applied by each traction unit comprises two electronic force gauges 116, one for each traction unit. The load cell 114 is mounted on the sled member 100 and the hooks 104 are attached to the load cell so that the load applied by the traction unit 96 to the patient's body P is detected by the cell. A signal generated by the load cell 114, which is representative of the load applied by the traction unit 96, is received by the force gauge 116. The display means in the force gauge is responsive to the signal to provide a display indicating the load applied on a screen 116A. The electronic force gauge of the preferred embodiment is that manufactured by W. C. Dillon & Co., Inc of Santa Rosa, Calif. The Dillon gauge has been modified to separate the load cell from the casing carrying the display means. It is to be understood that the signal generated by such a force guage could be supplied to a microprocessor (not shown) controlling the traction unit motors 98 so that the application of a specific level of traction might be carried out automatically. Means in the form of a slip clutch (not shown) is provided for limiting the maximum traction which may be applied to the patient s body P to approximately 50 pounds.

OPERATION

The operation of the present invention is perhaps best understood in the context of treatment of a specific type of spinal disorder. However, it is to be understood that the apparatus 10 may be beneficially used for treatment of many other back ailments, including but not limited to scoliosis of the spine, which will not be specifically discussed. As previously set forth, a common cause of low back pain is a dislocation of the gel-like nuclear mass inside the disc causing the disc to protrude from between adjacent vertebrae. The protuberance impinges upon nerves around the spine causing pain, and reduces the normal flexibility between adjacent vertebrae. The attitude of adjacent vertebrae on either side of the disc is altered from general vertical alignment, such that the space between the vertebrae takes on a wedge shape. The apparatus 10 of the present invention may be employed to urge replacement of the nuclear mass and the disc between adjacent vertebrae.

The patient is first fitted with the thoracic vest V and the pelvic belt B. The therapist manually swings the platform 42 to its locked perpendicular position and activates the cylinder 34 through control box 37 to swing the table 12 to its vertical position (FIG. 2). The patient may stand on the platform 42 with his back to the table 12, and the therapist reactivates the cylinder 34 to swing the table to its horizontal position. The flexible back support 22 may be placed between the patient's back and the table 12 prior to swinging to the horizontal position. The therapist manually lowers the platform 42 to its horizontal position, and attaches the straps SB extending from the pelvic belt to the hooks 104 of the traction units 96 and the straps VS extending from the thoracic vest to the hooks 94 at the head of the table. The back support 22 is adjusted so that it is positioned under the area of the back to be treated, in this case, under the location of the protruding disc. The support member 24 is positioned so that the drum 48 is positioned above the area of the back to be treated, and locked into place.

Prior to treating the patient on the apparatus, the proper direction of motion for the back support 22 is determined by diagnostic evaluation of the patient carried out by x-ray, computerized tomography, magnetic resonance imaging or by other suitable procedures. For purposes of illustration, it will be assumed that the proper direction of motion dictates the apparatus configuration shown in FIG. 3. In that case, the lower pulley 53A on the leg 24A would be positioned by releasing detent pin 76, loosening bolt 78 and sliding sleeve 74 to the predetermined angle. The pulley 53A is then locked into position by the detent pin 76 and bolt 78. The therapist may choose any direction of movement (in 15° intervals) over a range of 180°, from lateral to vertical to the resultant of a lateral and vertical movement. The cable 62 is made to extend from the drum 48, under the fixed pulley 52A, over the upper pulley 53B and over the positioned lower pulley 53A to the back support 22. The back support 22 extends around the patient's body P, as described above. The metal ring 22E is positioned on the outer belt 22D so that it is adjacent the free end of the cable 62, and the cable is connected to the metal ring by the clasp 63. The lift mechanism 46 is activated to take up the slack in the cable 62.

Thereafter, traction is applied to the patient's spine by depressing the appropriate control buttons 109 to activate the traction unit motors 98. The load being applied to each side of the patient's body P is displayed on the screens 116A. Because the traction units 96 are independently controlled, different amounts of traction may be applied to each side of the spine. For instance, a greater amount of traction would be applied on the side laterally opposite the side of protuberance of the disc to promote repositioning the disc nucleus between the vertebrae. Of course the precise amount of traction will depend upon the size and build of the patient, the severity of the injury, and the informed judgment of a physician. Having applied the appropriate traction, the lift mechanism 46 is activated, extending and lifting the spine in a corrective direction, in this case, in the direction which facilitates repositioning of the disc nucleus between adjacent vertebrae. As spinal extension occurs, the traction is gradually reduced with the amount of lift and traction being varied in accordance to the comfortable tolerance of the patient and the judgment of the doctor.

When the lift and traction have been set at optimal levels, the therapist actuates the impulse means 80. This is done by grasping the lever 80C and moving it in the direction of arrow 84, shown in FIG. 4. As described above, this results in a brief, small magnitude displacement of the back support 22 and hence of the area of the back engaged by the back support. The magnitude of the brief displacement may be varied by adjusting the set screw 90 at the top of the support member 24 (FIG. 5). In the present embodiment, the greatest displacement which may be achieved is approximately one half inch. Again, the precise distance of displacement is judged by the doctor. Thus the apparatus 10 emulates the thrust which might be done by hand in manipulative therapy. However, through the application of mechanical apparatus, there is no requirement that the therapist have great strength or dexterity. Further, magnitude of the force applied and its direction may be more precisely controlled and accurately reproduced by the apparatus of the present invention.

After the impulse is applied, the patient typically remains in the position of lift and traction for several minutes. The traction is then released, first on the side of the disc protuberance, and then on the opposite side. The back support 22 is then gradually lowered to the table 12. The pelvic belt B and thoracic vest V are disconnected from the traction units 96 and hooks 94, respectively, and the back support 22 is disconnected from the cable 62. The support member 24 is then moved to the head of the table. The therapist positions the platform 42 in its perpendicular position and activates the cylinder 34 to swing the table 12 to the vertical position. As the table swings up, the patient may grasp the handles 44 mounted on the sides of the table to maintain balance.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. Apparatus for treatment of the back comprising,
support means for supporting a patient lying on his back,
traction means for placing the patient's spine in traction,
a back support adapted to be positioned underneath the patient's back,
means for effecting movement of the back support laterally toward one side or the other and vertically and in an inclined direction which is the resultant of a lateral and vertical movement,
a support member supporting said means for effecting movement of the back support,
said means for effecting movement of the back support comprising cable means adapted for connection to the back support and adjustable guide members selectively engageable with said cable means for guiding the movement of the back support in a selected direction, the guide members being mounted on said support member for movement with respect to the support member laterally of said support means.

2. Apparatus as set forth in claim 1 wherein said means for effecting movement of the back support further comprises drum means mounted on said support member for holding said cable means, said drum means being rotatable for reeling in and letting out said cable means thereby to move the back support.

3. Apparatus as set forth in claim 2 wherein the support member includes a first leg disposed generally adjacent one side of said support means and a second leg disposed generally adjacent the laterally opposite side of said support means, and wherein the guide members comprise pulley means including first pulley means on the first leg of the support member and second pulley means on the second leg of the support member, at least some of said first and second pulley means being adjustably positionable lengthwise of the support member legs, said cable means being adapted to extend from said drum means, over either of said first pulley means and said second pulley means to the back support, said cable means being adapted for connection to the back support.

4. Apparatus as set forth in claim 3 wherein the support member is positionable longitudinally of said support means.

5. Apparatus as set forth in claim 1 further comprising impulse means for selectively actuating a brief, small magnitude displacement of the back support thereby temporarily displacing an area of the patient's back engaged by the back support.

6. Apparatus as set forth in claim 5 wherein said impulse means is constrained to displace the back support in the same direction as said means for effecting movement of the back support.

7. Apparatus for treatment of the back comprising,
support means for supporting a patient lying on his back,
traction means for placing the patient's spine in traction,
a back support adapted to be positioned underneath the patient's back, and
means for effecting movement of the back support laterally toward one side or the other and vertically and in an inclined direction which is the resultant of a lateral and vertical movement,
said traction means being adapted to apply an independently controlled amount of traction to transversely opposite sides of the patient's spine.

8. Apparatus as set forth in claim 7 wherein said traction means comprises a pair of traction units and control means for independently controlling the traction units.

9. Apparatus as set forth in claim 8 further comprising means for detecting the traction applied by each traction unit and means for displaying the load applied in units of force, said detecting means comprising means for generating a signal representative of the load applied to the patient's body, said display means being responsive to said generating means to provide a display indicating the load applied.

10. Apparatus as set forth in claim 8 wherein each traction unit comprises a sled member and a motor for actuating motion of the sled member along a line generally parallel to the longitudinal extension of the support means, the sled member being adapted for connection to the patient s body.

11. Apparatus as set forth in claim 7 further comprising impulse means for selectively actuating a brief, small magnitude displacement of the back support thereby temporarily displacing an area of the patient's back engaged by the back support.

12. Apparatus for treatment of the back comprising,
support means for supporting a patient lying on his back,
a back support adapted to be positioned underneath the patient's back, and
impulse means for selectively actuating a brief, small magnitude displacement of the back support in a plane substantially perpendicular to the lengthwise extension of said support means thereby temporarily displacing an area of the patient's back engaged by the back support.

13. Apparatus as set forth in claim 12 further comprising means for placing the patient's spine in traction.

14. Apparatus as set forth in claim 12 further comprising means for effecting movement of the back support laterally toward one side or the other and vertically and in an inclined direction which is the resultant of a lateral and vertical movement.

15. Apparatus as set forth in claim 14 further comprising a support member supporting said means for effecting movement of the back support, and wherein said means for effecting movement of the back support comprises adjustable guide members adapted to guide the movement of the back support in a selected direction.

16. Apparatus as set forth in claim 15 further comprising cable means adapted for connection to the back support and drum means mounted on said support member for holding said cable means, said impulse means being adapted to actuate said brief, small amplitude displacement of the back support through said cable means.

17. Apparatus as set forth in claim 16 wherein said drum means is mounted on a platform pivotally mounted on the support member, and wherein said impulse means comprises means for pivoting the platform resulting in a brief, small magnitude displacement of the drum.

18. Apparatus for treatment of the back comprising,
support means for supporting a patient lying on his back,
a back support adapted to be positioned underneath the patient's back,
impulse means for selectively actuating a brief, small magnitude displacement of the back support thereby temporarily displacing an area of the patient's back engaged by the back support, and
traction means for placing the patient's spine in traction, said traction means being adapted to apply an independently controlled amount of traction to transversely opposite sides of the patient's spine.

19. Apparatus as set forth in claim 18 wherein said traction means comprises a pair of traction units and control means for independently controlling the traction units.

20. Apparatus as set forth in claim 19 further comprising means for detecting the traction applied by each traction unit and means for displaying the load applied in units of force, said detecting means comprising means for generating a signal representative of the load applied to the patient's body, said display means being responsive to said generating means to provide a display indicating the load applied.

* * * * *